United States Patent
Peco

(10) Patent No.: US 11,598,025 B2
(45) Date of Patent: Mar. 7, 2023

(54) APPARATUSES AND METHODS FOR PLANT PROCESSING

(71) Applicant: CANOPY GROWTH CORPORATION, Smiths Falls (CA)

(72) Inventor: Phil Peco, Smiths Falls (CA)

(73) Assignee: CANOPY GROWTH CORPORATION, Smiths Falls (CA)

( * ) Notice: Subject to any disclaimer, the term of this patent is extended or adjusted under 35 U.S.C. 154(b) by 740 days.

(21) Appl. No.: 16/455,995

(22) Filed: Jun. 28, 2019

(65) Prior Publication Data

US 2020/0002846 A1      Jan. 2, 2020

Related U.S. Application Data

(60) Provisional application No. 62/693,165, filed on Jul. 2, 2018.

(51) Int. Cl.
*D01B 1/22* (2006.01)
*A01D 82/02* (2006.01)
(Continued)

(52) U.S. Cl.
CPC .............. *D01B 1/22* (2013.01); *A01D 82/02* (2013.01); *B02C 23/08* (2013.01); *D01B 1/32* (2013.01)

(58) Field of Classification Search
CPC ... D01B 1/00; D01B 1/02; D01B 1/10; D01B 1/22; D01B 1/24; D01B 1/30; D01B 1/32;
(Continued)

(56) References Cited

U.S. PATENT DOCUMENTS

| 4,773,434 A * | 9/1988 | Miyake .................. A01D 45/16 |
| --- | --- | --- |
| | | 131/319 |
| 5,044,115 A * | 9/1991 | Richardson .............. A01G 5/00 |
| | | 47/1.01 R |

(Continued)

FOREIGN PATENT DOCUMENTS

| CA | 2985587 A1 * | 1/2018 | ............... A01G 3/00 |
| --- | --- | --- | --- |
| CA | 2985587 A1 | 1/2018 | |

(Continued)

OTHER PUBLICATIONS

International Search Report and Written Opinion issued in PCT/CA2019/050901, dated Aug. 30, 2019, 11 pages.

*Primary Examiner* — Gene O Crawford
*Assistant Examiner* — Muhammad Awais
(74) *Attorney, Agent, or Firm* — Stinson LLP

(57) ABSTRACT

An apparatus with a projection defining first and second openings and a channel between the openings. An interior surface adjacent the channel tapers inwardly from the first opening to the second opening, and a shearing edge is positioned adjacent the second opening. A method of using the apparatus to separate protuberances of a plant from an elongate portion of the plant by pulling the elongate portion through the channel. Another apparatus with first and second counter-rotating rollers. Each roller having alternating projecting portions and valleys and oriented so that projecting portions of one roller are aligned with valleys of the other roller as the rollers rotate. A method of using the rollers to deform an elongate portion of a plant between the projecting portions of one roller and the valleys of the other roller.

17 Claims, 4 Drawing Sheets

(51) Int. Cl.
*B02C 23/08* (2006.01)
*D01B 1/32* (2006.01)

(58) Field of Classification Search
CPC ...... A01G 2003/005; A01G 3/04; A01G 5/00; A01D 82/02; A01D 46/02; A01D 45/06; A01H 6/28; B02C 23/08; B07B 1/00; B07B 13/04; B07B 2220/00
USPC ....................................................... 209/618
See application file for complete search history.

(56) References Cited

U.S. PATENT DOCUMENTS

| | | | |
|---|---|---|---|
| 6,382,426 B1 * | 5/2002 | Nicholson | B07B 1/15 99/635 |
| 7,338,229 B1 * | 3/2008 | Kuo | E01F 9/688 404/9 |
| 2002/0144457 A1 * | 10/2002 | Harrison, Jr. | A01G 5/00 47/1.01 R |
| 2015/0040734 A1 * | 2/2015 | Harris | A01G 5/06 83/72 |
| 2015/0082760 A1 * | 3/2015 | Zentner | A01D 45/021 56/62 |
| 2018/0077866 A1 * | 3/2018 | Perez | A01D 43/086 |
| 2018/0100844 A1 * | 4/2018 | Hilscher | G01N 33/025 |
| 2018/0116117 A1 * | 5/2018 | Lutz | B02C 4/08 |

FOREIGN PATENT DOCUMENTS

| | | | | |
|---|---|---|---|---|
| CA | 3001150 A1 | * | 3/2018 | ............ A24B 5/06 |
| CA | 3001150 A1 | | 3/2018 | |
| CN | 202232233 U | * | 5/2012 | |
| CN | 202232233 U | | 5/2012 | |
| CN | 107034519 A | * | 8/2017 | |
| EP | 0332730 A1 | * | 9/1989 | |
| FR | 2631776 A1 | * | 12/1989 | |
| WO | 97/45573 A1 | | 12/1997 | |
| WO | WO-9745573 A1 | * | 12/1997 | ........... A01D 45/065 |

* cited by examiner

APPARATUSES AND METHODS FOR PLANT PROCESSING

CROSS-REFERENCE TO RELATED APPLICATIONS

This application is based on and claims priority to U.S. Provisional Application Ser. No. 62/693,165, filed on Jul. 2, 2018, which is incorporated herein by reference in its entirety.

STATEMENT REGARDING FEDERALLY SPONSORED RESEARCH OR DEVELOPMENT

Not applicable.

STATEMENT REGARDING JOINT RESEARCH AGREEMENT

Not applicable.

BACKGROUND OF THE INVENTION

1. Field of the Invention

This disclosure relates generally to agricultural apparatuses and methods and more specifically to apparatuses and methods for processing a plant.

2. Description of Related Art

The use of cannabis for medicinal purposes has increased in recent years. A cannabis plant includes flowering parts that must be gently removed from a remainder of the cannabis plant (i.e., the stems) during harvesting. Such flowering parts are also called buds and comprise the parts that are the richest in cannabinoids. Thus, it is desirable to separate them from the stems and large fan leaves that are lower in cannabinoid concentration. Machines used to separate such stems and flowering parts are commonly called "bud buckers" or "bud strippers."

Current machines designed for harvesting cannabis typically include a pair of counter-rotating rollers that grip a main stem of the plant and pull it through an aperture in a faceplate that is sized such that the stem can freely pull through but the buds, which usually have a larger diameter, are sheared off from the stem as it is pulled through the aperture in the plate.

One problem encountered with faceplates having simple apertures is that buds are easily crushed by the perpendicular shearing action resulting in poor quality product. A solution to this problem is attaching a short perpendicular tube, matching the diameter of the aperture to the faceplate so the buds are sheared off by a thin edge of the tube instead of a flat face of the faceplate. However, because cannabis tends to be resin bearing, the inner portions of the tubes can become coated with sticky resin from the plants as the stems pass therethrough, thus increasing the force that needs to be applied in order to pull the stem through the aperture. Eventually, the required force can become so great that the feed rollers can lose grip of the stems or the stems can break as a user tries to pass the stems through the faceplate.

Another problem encountered in cannabis harvesting is a need to dispose of the non-flowering part of the plant, i.e., the stripped stems. Currently available machines use relatively smooth rubber covered rollers that leave the stripped stem in one straight piece with smaller branching stems radiating from it. This material does not pack efficiently and must be crushed in a separate operation in order to facilitate efficient disposal. Moreover, the rubber coatings can become fouled with resin, requiring constant cleaning, and eventually, the chemical constituents in the resin can degrade the elastomers thus requiring constant replacement

BRIEF SUMMARY OF THE INVENTION

One exemplary embodiment of an apparatus for processing a plant includes a base and a projection that is coupled with and extends outward from the base. The projection defines a first opening and a second opening, and a channel extends through the projection from the first opening to the second opening. The projection has an interior surface positioned adjacent the channel, and the interior surface tapers inwardly from the first opening to the second opening. The projection has a shearing edge positioned adjacent the second opening. The shearing edge may be configured for shearing protuberances of a plant (e.g., flowering buds) from an elongate portion of a plant (e.g., a stem) as the elongate portion is pulled through the projection from the second opening to the first opening. The tapered interior surface may limit contact between the elongate portion of the plant and the interior surface to limit the transfer of plant material (e.g., resin) to the interior surface and accumulation of such plant material on the interior surface.

The interior surface may be frustoconical with the first opening having a first diameter and the second opening having a second diameter that is smaller than the first diameter. The apparatus may further include a pair of counter-rotating rollers positioned adjacent the first opening of the projection, wherein the rollers are configured to engage an elongate portion of a plant positioned between the rollers, and wherein the rollers are configured to rotate to pull the elongate portion of the plant through the channel of the projection. Each of the rollers may have an outer surface with alternating projecting portions and valleys.

A method for processing a plant in accordance with another aspect of this disclosure includes use of an apparatus having a projection defining a first opening and a second opening. A channel extends through the projection from the first opening to the second opening. The projection has an interior surface positioned adjacent the channel, and the interior surface tapers inwardly from the first opening to the second opening. The projection has a shearing edge positioned adjacent the second opening. The plant has an elongate portion and a plurality of protuberances joined to the elongate portion. The method includes pulling the elongate portion of the plant through the channel from the second opening to the first opening such that a plurality of the protuberances of the plant are separated from the elongate portion by the shearing edge of the projection before the protuberances enter the channel. The elongate portion of the plant may be a stem, and the protuberances may be flowering buds of the plant. The plant may be cannabis.

Another exemplary embodiment of apparatus for processing a plant includes a first roller and a second roller. The first roller having a first outer surface with a first set of alternating projecting portions and valleys, and the second roller having a second outer surface with a second set of alternating projecting portions and valleys. The first roller is configured to rotate in a first direction, and the second roller is configured to rotate in a second direction that is opposite to the first direction. The first roller is oriented with respect to the second roller so that as the first and second rollers rotate one of the projecting portions on the first roller is positioned adjacent one of the valleys on the second roller or one of the projecting portions on the second roller is positioned adjacent one of the valleys on the first roller. The rollers may be configured to engage and pull an elongate portion of a plant through a gap between the rollers. The rollers may further crush, compact, deform, and or curl the elongate portion of the plant as it is engaged and pulled by the rollers.

A method for processing a plant in accordance with another aspect of this disclosure includes use of an apparatus having first and second rollers each comprising an outer surface with alternating projecting portions and valleys. The method includes simultaneously rotating the rollers in opposite directions so that the projecting portions of the first roller are successively positioned adjacent the valleys of the second roller and the projecting portions of the second roller are successively positioned adjacent the valleys of the first roller; positioning an elongate portion of a plant between the rotating rollers; and deforming the elongate portion of the plant between the projecting portions of the first roller and the valleys of the second roller and between the projecting portions of the second roller and the valleys of the first roller. The elongate portion of the plant may be a stem, and the plant may be cannabis.

The apparatuses and methods described above may be used to harvest a cannabis plant in a manner that minimizes damage to the desired harvested flowering buds of the plant, and which efficiently packs the residual parts of the plant (i.e., the stems and leaves) for further processing or disposal.

Additional aspects of the invention, together with the advantages and novel features appurtenant thereto, will be set forth in part in the description which follows, and in part will become apparent to those skilled in the art upon examination of the following, or may be learned from the practice of the invention. The objects and advantages of the invention may be realized and attained by means of the instrumentalities and combinations particularly pointed out in the appended claims.

DETAILED DESCRIPTION OF EXEMPLARY EMBODIMENTS

In accordance with the principles of the present disclosure, apparatuses and methods for processing a plant are disclosed herein. The apparatuses and methods described herein may be used to process any type of suitable plant, which may include, for example, plants that have an elongate portion (e.g., a stem or a bine) and a plurality of protuberances joined to the elongate portion (e.g., buds, flowers, or flowering buds). As described herein, the apparatuses and methods may be configured to separate the protuberances from the elongate portion. The apparatuses and methods may also be configured to crush, compact, deform, and/or curl the elongate portion for disposal or further processing. The apparatuses and methods may be configured for processing cannabis plants by separating flowering buds of the cannabis plants from stems of the plants and by crushing, compacting, deforming, and/or curling the stems to facilitate disposal and/or further processing.

Figure 1:
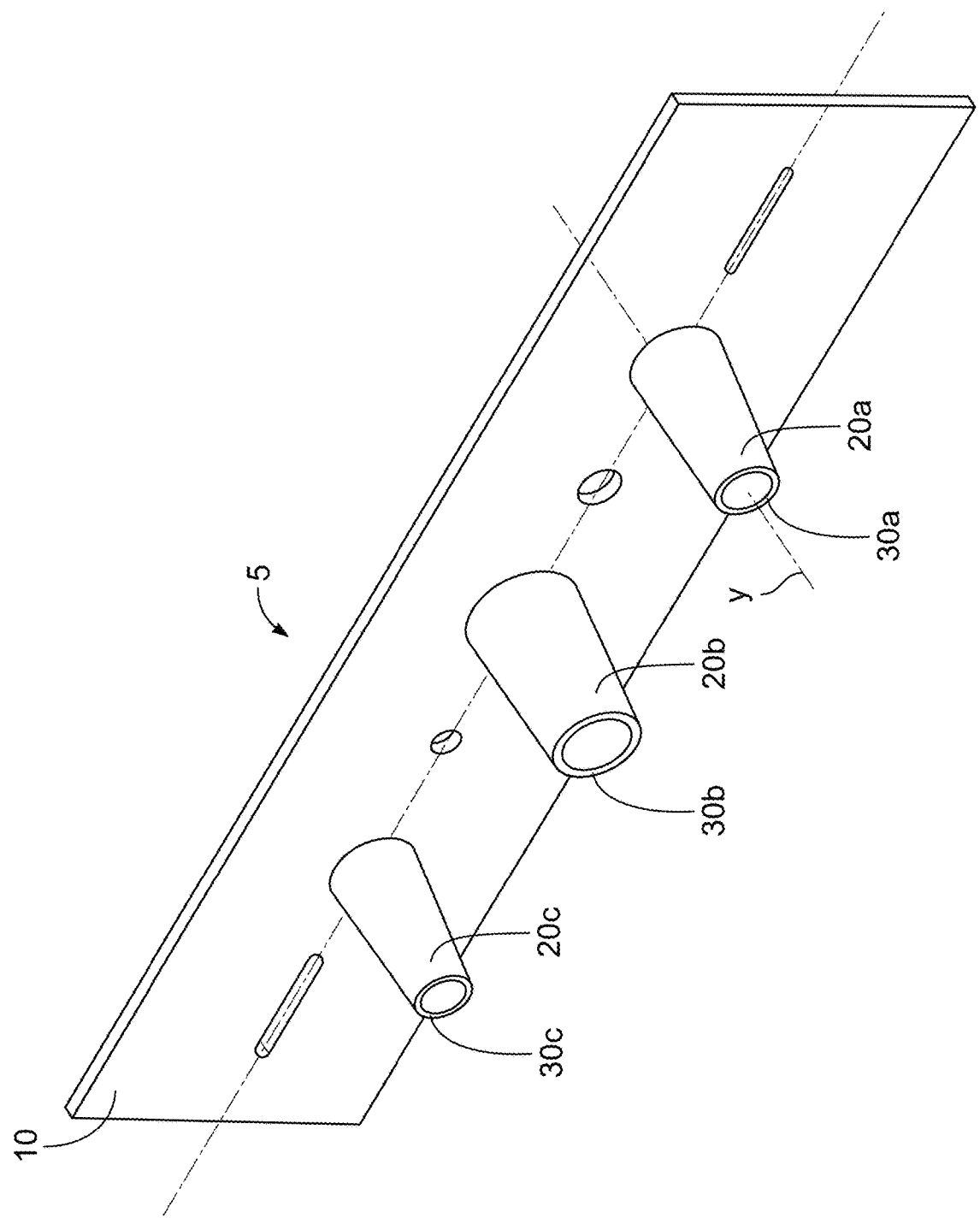
FIG. 1 is a perspective view of an apparatus for processing a plant in accordance with one exemplary embodiment described herein.

One exemplary embodiment of an apparatus for processing a plant is identified generally as 5 in FIG. 1. Apparatus 5 includes a base 10 (or faceplate) to which is joined three projections 20*a-c* that extend outward from the base 10. Projections 20*a-c* are shown as hollow truncated cone shaped projections. Each of projections 20*a-c* has a shearing edge 30*a-c* designed to separate protuberances of a plant from an elongate portion of the plant that passes through the projections 20*a-c*. Apparatus 5 may be used with other aspects of a system for processing a plant that are described herein.

Figure 2:
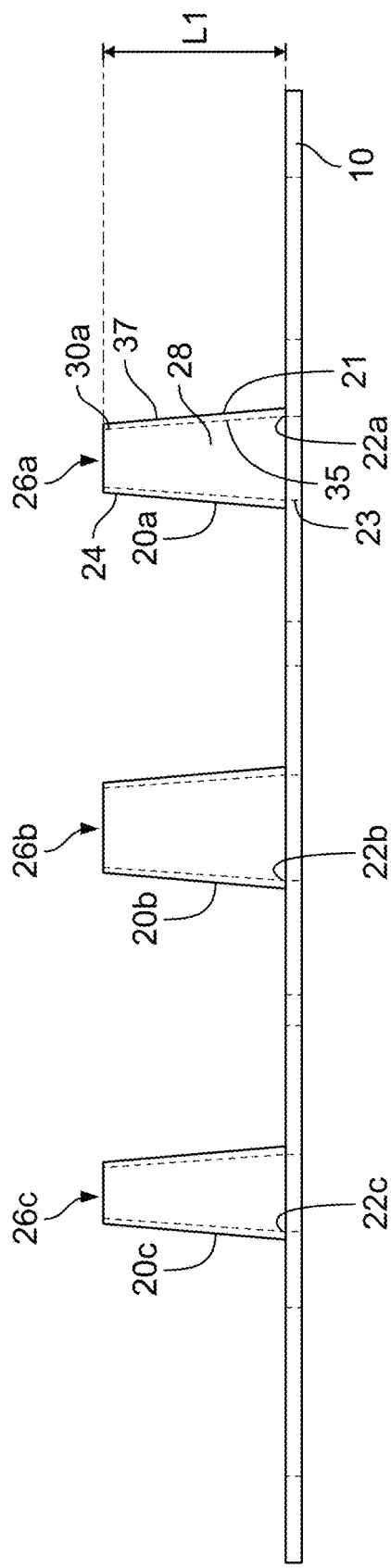
FIG. 2 is a bottom plan view of the apparatus of FIG. 1.

Projections 20*a-c* have a substantially similar structure; accordingly, only projection 20*a* is described in detail herein. Referring to FIG. 2, projection 20*a* includes a first end 21 that is attached to base 10 and a second end 24 that is spaced apart from base 10. First end 21 includes a first opening 22*a* that is aligned with an opening 23 through base 10. Second end 24 includes a second opening 26*a*, and shearing edge 30*a* is positioned around second opening 26*a*. An interior surface 35 of projection 20*a* extends from first end 21 to second end 24 and defines a channel 28 extending through the projection 20*a*. The channel 28 extends through the projection 20*a* from the first opening 22*a* to the second opening 26*a*. The interior surface 35 is tapered and tapers inwardly as it extends from the first end 21 to the second end 24. As shown, interior surface 35 is frustoconical and tapers radially inward as it extends from the first end 21 to the second end 24. Projection 20*a* is also shown as having an outer surface 37 that is frustoconical and that extends from the first end 21 to the second end 24.

Although projection 20*a* is shown as having an interior surface 35 that is frustoconical, interior surface 35 may have any shape that tapers inwardly from first end 21 to second end 24. For example, interior surface 35 may be frustopyramidal. Further, although first end 21 of projection 20*a* is shown as being joined to base 10, any portion of projection 20*a* between first end 21 and second end 24 may be joined to base 10 with shearing edge 30*a* being spaced apart from base 10.

Elongate portions of a plant (e.g., stems of a cannabis plant) may be inserted through second opening 26*a*, channel 28, and first opening 22*a* of projection 20*a* (and through second openings 26*b-c* and first openings 22*b-c* of projections 20*b-c*) and into engagement with an apparatus for pulling the elongate portions through the channel 28 (e.g., the apparatus 100 described below in connection with FIGS. 4 and 5). The pulling apparatus may be located on an opposite side of base 10 relative to a user inserting the elongate portions into second openings 26*a-c*, as shown in FIG. 6. The pulling apparatus (e.g., apparatus 100) may pull the elongate portions through projections 20*a-c* while protuberances of the plant (e.g., flowering buds) may be sheared from the elongate portions by contact of the protuberances and/or the elongate portions with shearing edges 30*a-c*. Thus, the protuberances of the plant may remain on a first side of base 10 where the user is located (i.e., adjacent the second openings 26*a-c*) and the elongate portions of the plant may be pulled through projections 20a-c such that the elongate portions are located on an opposite side of base 10 relative to the protuberances.

As indicated, projections 20a-c may be cone-shaped and such projections 20a-c may be attached to base 10 such that a longitudinal axis y (FIG. 1) of each projection is perpendicular or within 5-10 degrees of perpendicular relative to the surface of base 10 adjacent where the projection is joined. Base 10 may be a flat plate as depicted, which may be attachable to a remainder (not depicted) of the apparatus 5. As depicted, the larger diameter first end 21 of projection 20a may be located proximal to the base 10 and the smaller diameter second end 24 of projection 20a may be located distal to the base 10.

As an elongate portion of a plant is pulled through the channel 28, the tapered interior surface 35 of projection 20a provides enhanced clearance between the elongate portion of the plant and the interior surface 35. This clearance may prevent instances of contact between the plant and the interior surface 35 as the plant is pulled through the channel 28, which may lower the likelihood that substances from the plant will be transferred to and collect on the interior surface 35. For example, if the stem of a cannabis plant is pulled through the channel 28, the tapered interior surface 35 may avoid the collection of sticky resin on interior surface 35 that may otherwise occur in prior art devices as described above due to contact of the plants with the interior surface 35. Such reduction in resin adherence may allow apparatus 5 to operate more efficiently with less energy input and with less maintenance required. Further, it may result in higher quality flowering buds being separated from the cannabis stems. More specifically, the increased distance between opposing sides of interior surface 35 between smaller diameter second end 24 and larger diameter first end 21 may minimize contact between interior surface 35 and the cannabis plants. Such minimal contact also minimizes a deposition of a sticky residue that would result from a contact between the interior surface 35 and the cannabis plant as the plant passes through the projection 20a. This minimal contact, and thus drag, also conserves energy that would otherwise be associated with a smaller diameter passage.

The projections 20a-c may be formed of a same material as the base 10 such as stainless steel or a carbide (e.g., tungsten carbide inserts), titanium nitride coatings, or any other food grade acceptable, high strength, low wear, low friction material, with or without suitable non-stick coating, or they may be formed of a different material from the base 10. The projections 20a-c may be formed with the base 10 in a monolithic piece or the projections 20a-c may be attached to the base 10 such as by welding, soldering or brazing. In other examples, the projections 20a-c may be attached to the base 10 by threads, swaging, adhesive, or a bayonet attachment.

In an example, projections 20a-c may include longitudinal ridges on interior surface 35, which may inhibit sticking of stems of the plants to interior surface 35 since some or all of the surfaces of the valleys between the ridges may not contact the stems thereby inhibiting friction between interior surface 35 and the stems. This may allow the stems to pass more easily through projections 20a-c while minimizing a buildup of resin on the interior surface. In another example, interior surface 35 may be dimpled or have other patterns to minimize such friction and a buildup of resin. In a further example, a nozzle may be located to spray liquid lubricant on the interior surface 35 of projections 20a-c to inhibit friction between the stems and the interior surface.

Shearing edges 30a-c of projections 20a-c may be beveled and may be symmetrical, unsymmetrical, scalloped, sloped or V-shaped to facilitate a shearing of the flowering buds and parts of a cannabis plant from the stems thereof. Referring to projection 20a, shearing edge 30a may be located at a point of smaller diameter second end 24 furthest from base 10 or shearing edge 30a may be spaced from such a furthest end of smaller diameter second end 24 toward base 10. Shearing edge 30a may also be formed by cutting a front surface of smaller diameter second end 24 along a plane or several planes not perpendicular to a longitudinal axis y of the projection 20a such that when a stem is introduced into the projection 20a a leading point or portion of shearing edge 30a may contact the plant before a remainder of the projection 20a. More specifically, the shearing edge 30a may be shaped such that it is not located at a uniform distance from base 10.

Base 10 may be a flat plate as described above and may be any shape including rectangular, square, or circular. Base 10 may be easily removable (e.g., connectable using bolts, screws or other removable fasteners) from the remainder of apparatus 5 for cleaning or replacement. Also, base 10 may be concave or convex.

Figure 3:
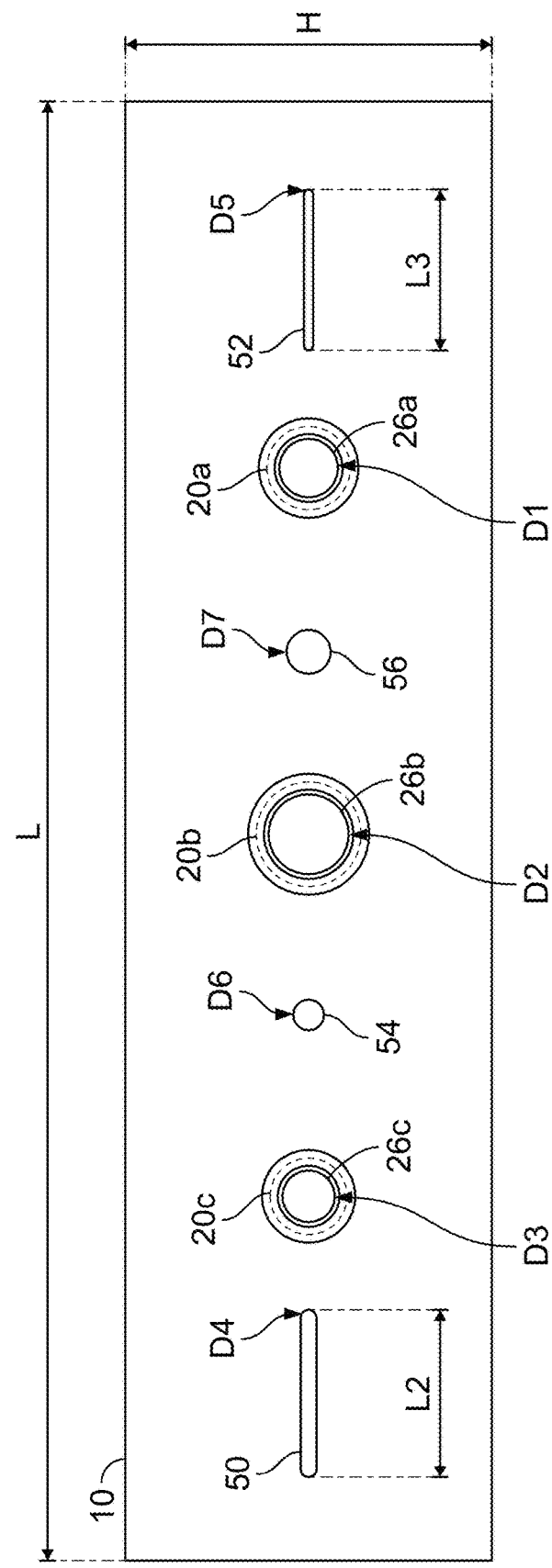
FIG. 3 is a front elevational view of the apparatus of FIG. 1.

In one embodiment and referring to FIG. 3, base 10 may have a longitudinal dimension or length L of approximately 12 in., for example, and a height H of approximately 3 inches. The smaller diameter second openings 26a-c of projections 20a-c may have diameters D1, D2, and D3. The diameters D1, D2, and D3 may be sized so that they do not allow protuberances of a desired plant to pass through the projections 20a-c (i.e., the protruberances are sheared from an elongate portion of the plant by shearing edges 30a-c). In one embodiment, the diameters D1, D2, and D3 may be between approximately 0.25 to 0.625 inches, between approximately 0.25 to 0.5 inches or between approximately 0.375 to 0.438 inches. As shown in FIG. 3, diameters D1, D2, and D3 may have different sizes designed to receive plants having different sized protruberances. D1 may be approximately 0.438 inches, D2 may be approximately 0.625 inches, and D3 may be approximately 0.375 inches. The larger diameter first openings 22a-c of projections 20a-c may have a diameter that is between approximately 0.1 to 0.75 inches larger than the smaller diameters D1, D2, and D3 of the respective projection 20a-c, or between approximately 0.25 to 0.5 inches larger. In one exemplary embodiment, the diameter of the first openings 22a-c may be between approximately 0.5 to 1 inches or approximately 0.625 inches. The diameters of the projections 20a-c referenced above may vary based on the plants or stems to be processed and other factors. Base 10 or a separate face plate may also be shaped to direct flowering points sheared from the stems of a plant in a particular direction such as a collection area, a conveyor or other desired location. The indicated openings 22a-c and 26a-c of the projections 20a-c may vary in size based on a size of the plants being input and the force applied to pull plants through the projections. Further, a length of the projections 20a-c may vary and may be designed in conjunction with the diameter of the smaller second openings 26a-c to enhance the safety of a user by minimizing a likelihood of the user contacting the mechanism for pulling the plants through the projections 20a-c. In one exemplary embodiment, a length of the projections 20a-c, L1 (FIG. 2), may be between approximately 1 to 1.5 inches or approximately 1 inch.

As shown in FIG. 3, base 10 further includes two slots 50 and 52. Slot 50 may have a length L2 of approximately 1.375 inches and rounded ends with a diameter D4 of approximately 0.125 inches. Slot 52 may have a length L3 of approximately 1.3 inches and rounded ends with a diameter D5 of approximately 0.063 inches. Base 10 further includes two openings 54 and 56 with opening 54 positioned between projections 20*c* and 20*b* and opening 56 positioned between projections 20*b* and 20*a*. Opening 54 may have a diameter D6 of approximately 0.25 inches, and opening 56 may have a diameter D7 of approximately 0.375 inches.

A guard plate (not depicted) may be connected to base 10. The guard plate may be fastened in front of projections 20*a-c* and parallel to base 10 to prevent hand contact of the user with projections 20*a-c*. Such guard plate may have a plurality of apertures aligned with the projections 20*a-c* with such apertures being larger than second openings 26*a-c* of projections 20*a-c*. The guard plate apertures may include cone-shaped protuberances where a smaller diameter of each cone is larger than second openings 26*a-c* of each of projections 20*a-c* with a small diameter opening of the guard plate aperture facing second openings 26*a-c* at shearing edges 30*a-c* of each of projections 20*a-c*. The guard plate may also have a lockout system to prevent operation of apparatus 5 if the guard plate is not properly installed. Also, the guard plate may be a solid plate or may be formed of wire in a similar manner to that of a fan blade guard.

Figure 5:
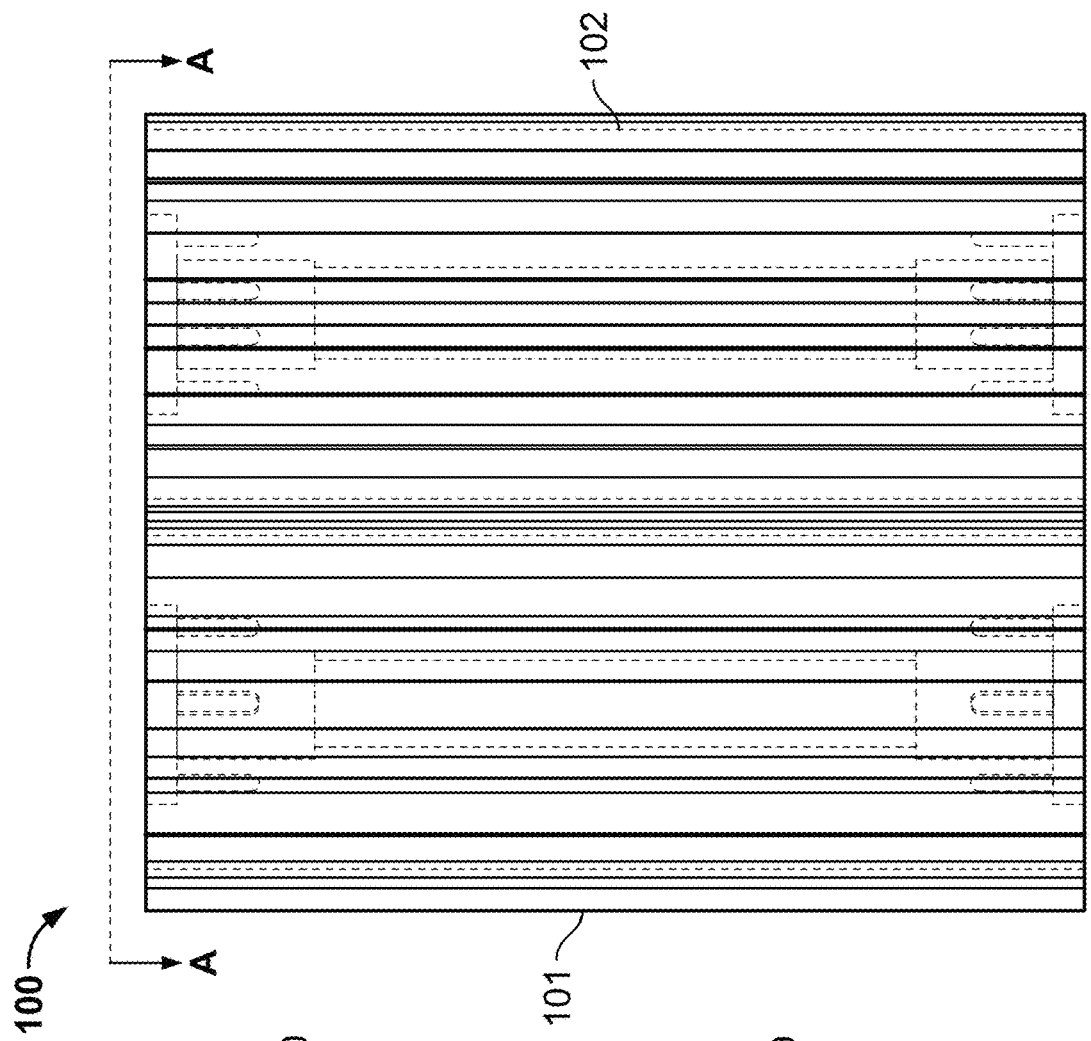
FIG. 5 is a rear elevational view of the apparatus of FIG. 4.
Figure 4:
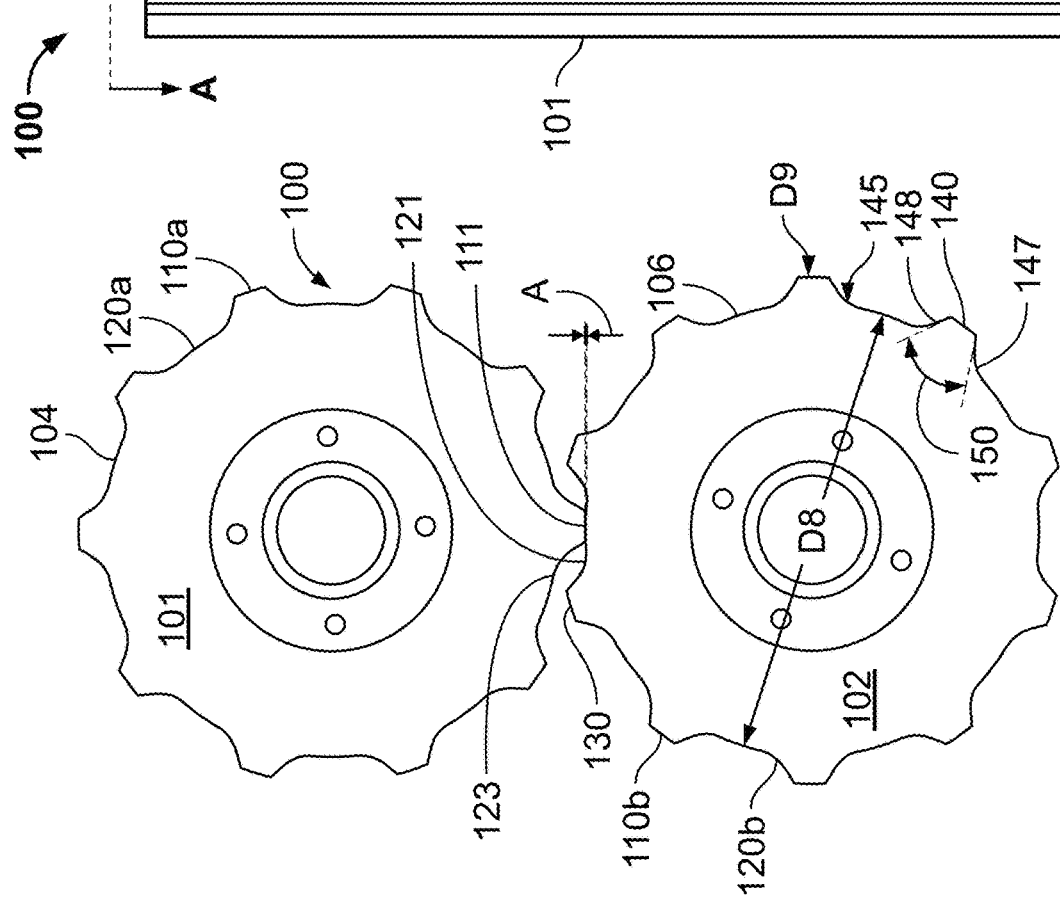
FIG. 4 is a side cross-sectional view of another apparatus for processing a plant in accordance with an exemplary embodiment described herein.
Figure 6:
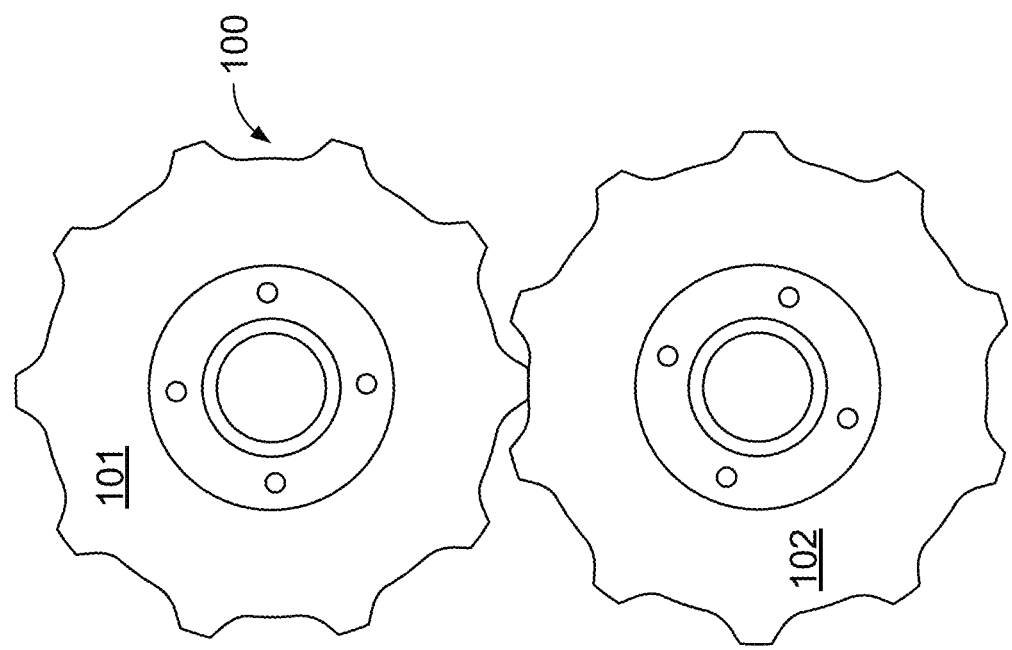
FIG. 6 is a side elevational view of the appartuses for processing a plant shown in FIGS. 1 and 4.
Figure 6:
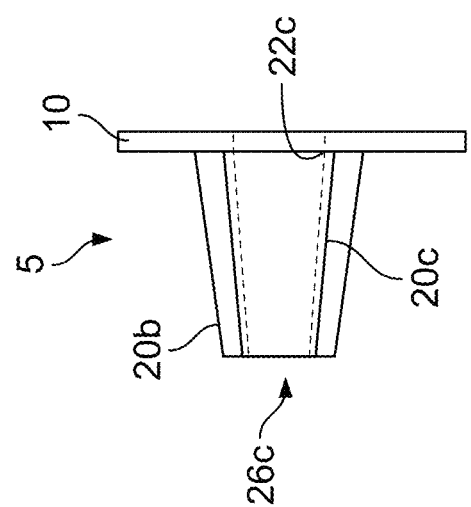

Referring now to FIGS. 4 and 5, an exemplary embodiment of an apparatus for processing a plant is identified generally as 100. Apparatus 100 is designed to engage, pull, and at least partially crush, compact, deform, and/or curl an elongate portion of a plant. Apparatus 100 may be used in connection with apparatus 5 to pull an elongate portion of a plant through projections 20*a-c*. When used in this manner, apparatus 100 is positioned behind base 10 on the opposite side of base 10 as projections 20*a-c* and adjacent first openings 22*a-c*, as shown in FIG. 6.

As shown in FIG. 4, apparatus 100 includes a set of cogged interlocking feed rollers 101 and 102 that may render a spent elongate portion of a plant (e.g., a stem that has passed through apparatus 5 and been separated from the flowering parts) into a compact crushed soft mass that can be easily compacted for disposal or further processed for fiber or extracted to yield additional cannabinoids or other cannabis derived phytochemicals. The rollers 101 and 102 may be of equal diameter, or may differ in diameter so that the spent elongate portion of the plant naturally curls up into a more compact shape. Rollers 101 and 102 are counter-rotating so that as the rollers 101 and 102 rotate they are able to engage and pull an elongate portion of a plant toward and through a gap A between the rollers. Roller 101 rotates in a first direction and roller 102 rotates in a second direction that is opposite to the first direction.

Rollers 101 and 102 have outer surfaces 104, 106 with outwardly projecting portions 110*a-b* separated from each other by valleys 120*a-b* such that the projecting portions 110*a-b* and valleys 120*a-b* alternate around the circumference of the rollers 101 and 102. The difference in diameter between projecting portions 110*a-b* and valleys 120*a-b* facilitates a bending or crumpling of elongate portions of plants (e.g., stems separated from flowering parts as the stems pass through apparatus 5 including projections 20*a-c*). For example, the roller 101 of apparatus 100 may include a contacting projecting portion 111 of projecting portions 110*a* which may force a portion of an elongate portion of a plant against or toward a valley 121 of valleys 120*b* on roller 102 of apparatus 100. Roller 102 may include an upwardly projecting portion 130 of projecting portions 110*b* which may force other portions of the elongate portion of the plant against or toward a valley 123 of valleys 120*a* of roller 101. Such contact of the projecting portions 110*a-b* with the elongate portions of the plant to force such elongate portions toward an opposite roller 101 or 102 may bend, break or otherwise reduce a size of the elongate plant portions to facilitate storage thereof.

Rollers 101 and 102 may be formed of any suitable material including stainless steel, tungsten carbide, or include a titanium nitride coating or treatment, and may be formed of or coated with a material to conform with food grade regulations such as per Health Canada, USDA, or various State regulations. Rollers 101 and 102 may have a bare metal surface to contact plant material (e.g., cannabis stems) during operation or such rollers may be coated with a non-stick coating to facilitate separation between the rollers 101 and 102 and the plant material. The rollers 101 and 102 may also be coated with a chemically resistant elastomeric coating, an anodized coating or a wear-resistant coating. The rollers 101 and 102 may have a dimpled outer surface to minimize friction between the plant material and rollers as described above relative to interior surfaces of projections 20*a-c*, for example.

To facilitate maintenance, the rollers 101 and 102 may also be removable without the use of tools, such as utilizing keyed shafts or spline shafts, for example. Further, a wall plate of apparatus 100 may include flange-mounted bearings that receive ends of the rollers 101 and 102 or shafts on which the rollers are mounted. The wall plate may be on linear rails to allow the plate to be unlocked and slid out of position thereby exposing the rollers 101 and 102 on cantilevered shafts. Such rollers 101 and 102 may then be removed and repaired or replaced and the wall plate slid back to its original position.

In an example, there may be a gap with a distance A (FIG. 4) between rollers 101 and 102 as the rollers 101 and 102 rotate. The gap distance A may be at least 0.1 inches or approximately 0.15 inches. As shown in FIG. 4, the gap distance A represents the distance between the projecting portion 111 of roller 101 and the valley 121 of roller 102 when the projecting portion 111 is aligned with the valley 121 and extends in a direction toward the central axis of roller 102. The gap distance A may further represent the distance between any of the projecting portions 110*a* of roller 101 when they are aligned with one of the valleys 120*b* of roller 102, and the distance between any of the projecting portions 110*b* of roller 102 when they are aligned with one of the valleys 120*a* of roller 101. The diameter and speed of rollers 101 and 102 may be configured so that as the rollers 101 and 102 rotate one of the projecting portions 110*a* of roller 101 enters and is aligned with one of the valleys 120*b* of roller 102, and then as that projecting portion 110*a* exits the valley 120*b*, one of the projecting portions 110*b* of roller 102 enters and is aligned with one of the valleys 120*a* of roller 101. This process may continue in a successively alternating manner as the rollers 101 and 102 rotate. Rollers 101 and 102 may have a valley diameter D8 that extends from a valley 120*a-b* on one side of a roller 101, 102 to a valley 120*a-b* on the opposite side of the roller 101, 102. The diameter D8 may be between approximately 4.5 to 5 inches, or approximately 4.7 inches or 4.709 inches. The rollers 101 and 102 may be connected to shafts driven by a motor(s) in any of various ways of turning a shaft as will be known by those skilled in the art.

Each of projecting portions 110*a-b* may have a circumferential portion 140 positioned at an outer projecting portion diameter, D9, of the rollers 101, 102. The circumferential portion 140 may extend between first and second connecting portions 147, 148 that extend radially outward from valleys 120*a-b* on either side of the projecting portion 110*a-b*. A fillet 145 may transition from the first and second connecting portions 147, 148 to the adjacent valley 120*a-b*. The outer projecting portion diameter D9 of the rollers 101, 102 may be between approximately 5 to 5.5 inches or approximately 5.25 inches. The fillet 145 may have a radius of approximately 0.25 inches. An angle 150 between the first and second connecting portions 147, 148 may be between approximately 65-75 degrees or approximately 69 degrees. The indicated angles and dimensions may vary such that valleys 120*a-b* avoid contact with projecting portions 110*a-b* as rollers 101 and 102 rotate.

In operation, apparatus 5 and apparatus 100 may be used in connection with each other to separate protuberances of a plant (e.g., flowering buds) from an elongate portion of the plant (e.g., a stem). An operator causes rollers 101 and 102 to rotate in opposite directions, for example, by turning on a motor that is connected to shafts on which the rollers 101 and 102 are mounted. The motor may be directly connected to one of the rollers 101, 102 and connected via a reversing drive to the other of rollers 101, 102 such that the rollers 101 and 102 turn in opposite directions. An elongate portion of a plant is fed through one of the projections 20*a-c* from the second opening 26*a-c* to the first opening 22*a-c* and into contact with rollers 101 and 102 in the gap between the rollers. The rollers 101 and 102 engage the elongate portion of the plant and rotate in a direction that pulls the elongate portion of the plant through the projection 20*a-c* from the second opening 26*a-c* toward the first opening 22*a-c*. As the elongate portion of the plant is pulled through the projection 20*a-c*, protuberances joined to the elongate portion of the plant are sheared or separated from the elongate portion by the shearing edge 30*a-c* of the projection 20*a-c*. The elongate portion of the plant engaged by rollers 101 and 102 is crushed, compacted, deformed, and/or curled by the projecting portions 110*a-b* and valleys 120*a-b* of rollers 101 and 102. The protuberances of the plant that are separated from the elongate portion may be collected for further processing, and the crushed, compacted, deformed, and/or curled elongate portion may be discarded or sent for further processing as described above.

While several aspects of the present invention have been described and depicted herein, alternative aspects may be effected by those skilled in the art to accomplish the same objectives. Accordingly, it is intended to cover all such alternative aspects as fall within the true spirit and scope of the invention.

From the foregoing it will be seen that this invention is one well adapted to attain all ends and objectives hereinabove set forth, together with the other advantages which are obvious and which are inherent to the invention.

Since many possible embodiments may be made of the invention without departing from the scope thereof, it is to be understood that all matters herein set forth OPT or shown in the accompanying drawings are to be interpreted as illustrative, and not in a limiting sense.

While specific embodiments have been shown and discussed, various modifications may of course be made, and the invention is not limited to the specific forms or arrangement of parts and steps described herein, except insofar as such limitations are included in the following claims. Further, it will be understood that certain features and subcombinations are of utility and may be employed without reference to other features and subcombinations. This is contemplated by and is within the scope of the claims.

What is claimed and desired to be secured by Letters Patent is as follows:

1. An apparatus for processing a plant having an elongate portion and a plurality of protuberances joined to the elongate portion, the apparatus comprising:
    a base; and
    a projection coupled with and extending outward from the base, wherein the projection defines a first opening having a first size and a second opening having a second size smaller than the first size, wherein a channel extends through the projection from the first opening to the second opening, the channel is configured for the elongate portion of the plant to pass through the second opening before passing through the first opening, wherein the projection comprises an interior surface positioned adjacent the channel, wherein the interior surface tapers inwardly from the first opening to the second opening, and wherein the projection comprises a shearing edge positioned adjacent the second opening, wherein the shearing edge is configured to separate the protuberances from the elongate portion before the protuberances enter the channel through the second opening, and wherein the shearing edge is fixed relative to the first opening, the second opening, and the elongate portion of the plant as the elongate portion moves through the second opening.

2. The apparatus of claim 1, wherein the interior surface is frustoconical.

3. The apparatus of claim 1, wherein the first opening has a first diameter, and wherein the second opening has a second diameter.

4. The apparatus of claim 3, wherein the first diameter is between 0.5 to 1 inches, and wherein the second diameter is between 0.25 to 0.5 inches.

5. The apparatus of claim 3, wherein the first diameter is 0.625 inches, and wherein the second diameter is between 0.375 to 0.438 inches.

6. The apparatus of claim 1, wherein the interior surface has a length that is measured from the first opening to the second opening, and wherein the length is between 1 to 1.5 inches.

7. The apparatus of claim 1, wherein the interior surface is formed from a material selected from the group consisting of: stainless steel, carbide, tungsten carbide, titanium nitride, and combinations of any of the foregoing.

8. The apparatus of claim 1, wherein the interior surface comprises a non-stick coating.

9. The apparatus of claim 1, wherein a first end of the projection is mounted to the base, wherein the first opening is at the first end, wherein a second end of the projection is spaced apart from the base, and wherein the second opening is at the second end.

10. The apparatus of claim 1, further comprising a pair of counter-rotating rollers positioned adjacent the first opening of the projection, wherein the rollers are configured to engage the elongate portion of the plant positioned between the rollers, and wherein the rollers are configured to rotate to pull the elongate portion of the plant through the channel of the projection so that the elongate portion moves through the channel from the second opening toward the first opening.

11. The apparatus of claim 10, wherein each of the rollers comprises an outer surface with alternating projecting portions and valleys.

12. A method of processing a plant with an apparatus comprising a projection defining a first opening and a second opening, wherein a channel extends through the projection from the first opening to the second opening, wherein the projection comprises an interior surface positioned adjacent the channel, wherein the interior surface tapers inwardly from the first opening to the second opening, and wherein the projection comprises a fixed shearing edge positioned adjacent the second opening, the plant having an elongate portion and a plurality of protuberances joined to the elongate portion, the method comprising:

pulling the elongate portion of the plant through the channel from the second opening to the first opening such that a plurality of the protuberances of the plant are separated from the elongate portion by the fixed shearing edge of the projection before the protuberances enter the channel, and wherein the fixed shearing edge remains fixed relative to the elongate portion of the plant as the elongate portion moves through the second opening.

13. The method of claim 12, wherein the elongate portion of the plant comprises a stem, and wherein the protuberances comprise flowering buds of the plant.

14. The method of claim 13, wherein the plant comprises cannabis.

15. The method of claim 12, wherein the apparatus comprises a pair of counter-rotating rollers positioned adjacent the first opening of the projection, and further comprising inserting the elongate portion of the plant through the channel and between the counter-rotating rollers, and wherein the counter-rotating rollers pull the elongate portion of the plant through the channel as the rollers rotate.

16. The method of claim 15, wherein each of the rollers comprises an outer surface with alternating projecting portions and valleys, and further comprising deforming the elongate portion of the plant between projecting portions of one of the rollers and valleys of the other of the rollers.

17. The apparatus of claim 1, wherein the shearing edge positioned adjacent the second opening is continuous.

* * * * *